United States Patent [19]

Andelman

[11] Patent Number: 5,196,115
[45] Date of Patent: Mar. 23, 1993

[54] CONTROLLED CHARGE CHROMATOGRAPHY SYSTEM

[76] Inventor: Marc D. Andelman, 6 Nadine Rd., Framingham, Mass. 01701

[21] Appl. No.: 760,752

[22] Filed: Sep. 16, 1991

Related U.S. Application Data

[62] Division of Ser. No. 512,970, Apr. 23, 1990, abandoned.

[51] Int. Cl.$^5$ .............................................. B0D 15/08
[52] U.S. Cl. ............................... 210/198.2; 210/243; 210/541; 204/180.1; 204/299 R
[58] Field of Search ................... 204/180.2, 299 R; 210/635, 656, 747, 198.2, 243, 541

[56] References Cited

U.S. PATENT DOCUMENTS

| | | | |
|---|---|---|---|
| 2,555,487 | 6/1951 | Haugaard | 204/299 R |
| 2,741,591 | 4/1956 | Dewey | 204/299 R |
| 2,853,448 | 9/1958 | Heiskell | 204/180.1 |
| 3,324,026 | 6/1967 | Waterman | 204/299 R |
| 3,450,624 | 6/1969 | Natelson | 204/299 R |
| 3,451,918 | 6/1969 | Kolin | 204/299 R |
| 3,640,813 | 2/1972 | Nerenberg | 210/198.2 |
| 3,846,274 | 11/1974 | Gifford | 204/299 R |
| 3,847,773 | 11/1974 | Snyder | 204/299 R |
| 4,049,534 | 9/1977 | Posner | 204/299 R |
| 4,057,482 | 11/1977 | Candor | 204/299 R |
| 4,560,445 | 12/1985 | Hoover | 204/30 |
| 4,743,373 | 5/1988 | Rai | 210/198.2 |
| 4,769,191 | 9/1988 | Newman | 204/403 |

OTHER PUBLICATIONS

Bassler & Hartwick, "Electrically Conductive Stationary Phases for HPLC", Abstract from AICHE Meeting in San Francisco, Calif.
Antrim et al, "Electrochromatography-A Preliminary Study of the Effect of Applied Potential on a Carbonaceous Chromatographic Column", Anal. Chim. Acta., 1984, pp. 283-286.
Blaedel et al, "Continuous Quantitative Electrolysis", Anal. Chem., Jun., 1964, pp. 1245-1251, vol. 36, No. 7.
Strohl et al, "A Packed Graphite Cell for Thin-Layer Chromatography", Analytical Letters 2(8), 423-431 (1969).
Fujinaga, T., "Electrolytic Chromatography and Coulometric Detection with the Column Electrode", Pure Applied Chemistry, 25(1971) p. 709.
Herne et al, "Modified Graphites for Chelation and Ion Exchange", Analytical Chemistry, Dec. 1978, pp. 1954-1959, vol. 50, No. 14.
Stoner et al, "Absorption of Blood Proteins on Metals Using Capacitance Techniques", Journal of Physical Chemistry, Mar. 5, 1970, pp. 1088-1094, vol. 7, No. 5.
"KF for Electro Double Layer Capacitors", Toyobo Co. Bulletin, PCF 110 (Sep., 1984.
Waldrop, Science, vol. 247, Jan. 12, 1990, p. 161.

Primary Examiner—Ernest G. Therkorn
Attorney, Agent, or Firm—Richard P. Crowley

[57] ABSTRACT

A controlled charge chromatography column for the purification of a fluid containing materials, which column comprises a chromatographic column having an inlet for the introduction of a fluid to be purified and an outlet for the discharge of the purified fluid, and one or more concentrated materials and a flow-through capacitor disposed within the column between the inlet and the outlet, the flow-through capacitor means comprising a plurality of spirally wound, spaced apart layers to include a first electrically conductive backing layer, such as of graphite, and a first high surface area conductive layer secured to the backing layer, such as composed of porous carbon fibers and a non-conductive, porous spacer layer to electrically insulate the backing and conductive layer and to permit the flow of material therethrough, the flow-through capacitor to be connected to a DC power source to charge the respective conductive layers with different polarities whereby a fluid containing material through the column is purified by the electrically conductive stationary phase and the retention thereof onto the high surface area layer and permitting for example the purification of solutions of liquids, such as salt, and providing for the recovery of a purified liquid.

27 Claims, 1 Drawing Sheet

CONTROLLED CHARGE CHROMATOGRAPHY SYSTEM

This is a division of Ser. No. 512,970, filed Apr. 23, 1990, now abandoned.

BACKGROUND OF THE INVENTION

Chromatographic columns, particularly liquid chromatographic columns, have provided for the employment of an electrically conductive, stationary solid phase, and the preferential interaction of solutes in a fluid to be chromatographically separated with the solid, stationary phase, such as set forth in "Electrically Conductive Stationary Phases for HPLC"[1] issued by Barbara Bassler and Richard Hartwick, Abstract from the AICHE Meeting, San Francisco, Calif., Nov. 5–10, 1989, and in "Electrochromatography—A Preliminary Study of the Effect of Applied Potential On A Carbonaceous Chromatographic Column"[2], by Robert Antrim, Robert Scherrer and Alexander Yacynych, Anal. Chim. Acta., 164 (1984) 283. The above references describe an electron rich, porous, graphitic, carbon, stationary phase to act as a controlled potential surface to affect the resolution of solutes to be chromatographed in both polar and non-polar solvents. In such chromatographic columns as HPLC, the conductive packing is employed as one electrode and the surrounding metal tube of the column as the other electrode. These columns do not act as capacitors, since the voltage drop is generally entirely across the metal tube and insignificant across the claimed controlled potential surface to be modulated, so that little electrostatic absorption occurs.

In addition, electrically conductive stationary phases have been employed to deposit and strip solutes via electrolysis, see for example, "Continuous Quantitative Electrolysis"[3], W. J. Blaedel and J. H. Strohl, Anal. Chem., Vol. 36, No. 7, Jun., 1964; "A Packed Graphite Cell For Thin Layer Electrochemistry"[4], John Strohl and Thomas Polutanovich, Analytical Letters, 2(8), pp. 423–431 (1969); "Electrolytic Chromatography and Coulometric Detection With the Column Electrode"[5], Taitiro Fujinaga, Pure Applied Chemistry, 25 (1971) pp. 709–726; and "Modified Graphites for Chelation and Ion Exchange"[6], James Hern and John H. Strohl, Analytical Chemistry, Vol. 50, No. 14, Dec., 1978. In addition, capacitance techniques have been employed for the absorption of blood proteins on metals, as set forth by G. Stoner and S. Srinivasan, "Absorbtion of Blood Proteins on Metals Using Capacitance Techniques"[7], Journal of Physical Chemistry, Vol. 74, No. 5, pp. 1088–1094, Mar. 5, 1970. While electrolysis devices have been used to purify solutions, the devices affect purification by deposition and stripping electrochemically the material and not by electrostatic absorption.

U.S. Pat. No. 4,769,191[8], issued Sep. 6, 1988, describes an anode electrode of an electrolytic capacitor having a biochemically active layer embedded in the pores of the electrodes and that the electrodes change electrical properties by the presence of the chemical layers. This patent discloses using a biochemical layer and wherein analyte molecules replace other molecules from the biochemically active layer to effect the change in the dielectric properties of the electrodes, and this change is employed to measure the concentration of analyte molecules.

None of the above prior art references describe a device which affects absorption or resolution of solutes to be chromatographed via a high capacitance, combined with a flow-through configuration to allow the capacitor to function as a chromatographic system. It is desirable to provide for controlled charge chromatography system and method which employs a flow-through capacitor of high surface area material for both anode and cathode, to provide for a high efficiency, effective purifying system to modulate the absorption and/or resolution of ions and non-ionic solutes in polar and non-polar solvents.

SUMMARY OF THE INVENTION

The present invention relates to a controlled charge purification chromatography system and method, and more particularly relates to a chromatography system and method employing a flow-through capacitor of high electrical capacitance and high surface area absorption capacity.

A controlled charge chromatography system and method has been discovered which provides for the purification of solutes particularly in liquids containing both non-polar and polar materials, and which column comprises a column having an inlet for the introduction of the fluid to be purified and an outlet for the discharge of the purified fluid and one or more concentrated ionic materials. The controlled charge chromatographic column would also include a flow-through capacitor means disposed within the column between the inlet and the outlet so as to permit the flow of the fluid through the flow-through capacitor means, with the flow through capacitor means adapted to be connected to a DC power source to place charges on the film or layers in the capacitor. The flow-through capacitor may comprise a wide variety of configurations, such as for example a spirally wound capacitor. Such a spirally wound, flow-through capacitor would comprise a plurality of spaced apart layers with the layers generally axially aligned with the axis of the column, and the layers including a first non-conductive, porous spacer layer to define a flow channel to permit the flow of the feed fluid therethrough. For example, the spacer material may comprise a porous, inert-type material, such as woven, open space, synthetic material, such as nylon or fiberglass screen-like spacing material. A first electrically conductive backing layer may be composed of any electrically conductive material, such as a metal film for example of aluminum and/or more particularly of electrically conductive graphite. A first high surface area conductive layer material is secured or placed adjacent to the electrically conductive backing layer providing a very high surface area by virtue of a highly porous structure, and more particularly would comprise, for example, a compressed, activated carbon which is porous, or even more particularly, an activated carbon woven fibrous layer. The conductive layer may for example be wound in a spiral formation with the porous spacer material between the respective layers with six layers wound so as to provide for separate and opposite charges on two separate spirally wound backing layers.

Electrical leads may be connected to the first and second electrically conductive backing layers to a DC power source so that layers may be formed integrally with the backing layers. Generally, the flow-through capacitor may be prepared in spiral wound form by winding the respective layers about a central hollow perforated tube from inside to outside composed of a spacer layer, a backing layer, a high surface layer, a spacer layer, a backing layer and a high surface layer about a central plastic tube containing perforations therein and then sealed at the end by a resin, such as a thermoset epoxy resin, so as to provide for the introduction of the fluid material through the side of the spirally wound device, through the successive layers, and the purified fluid and the one or more ionic materials concentrated by the flow-through capacitor to be discharged from the other end of the central tube.

The controlled charge ionic purification chromatography system would thus include the chromatographic column containing the flow-through capacitor with a source of fluid, such as a liquid containing ionic materials, a pump means to pump or otherwise introduce the liquid material into the inlet of the chromatographic column, the column typically containing a cartridge-type flow-through capacitor, with the leads of the flow-through capacitor extending out of the column and secured to a DC power source, optionally to a logic device to program voltage on/off cycles, voltage gradients and reversal of polarity and otherwise to control electrically the capacitor and wherein the system also includes a collection disposed adjacent the outlet of the column whereby the purified material or the various eluting, concentrated ionic materials may be separately collected.

The method of the invention comprises flowing a fluid containing ionic material, either polar or non-polar solvents, through a flow-through capacitor in which the capacitor is a high capacitance, for example, over 1000 farads capacitance, and further which includes a surface active conductive layer secured to a backing and separated by a spacing layer from the adjacent high surface area layer and backing so as to increase the retention capacity and electrical capacitance of the capacitor. The charge on the capacitor is controlled so as to attract and hold charged molecules in the fluid by virtue of the charge-holding ability implicit in the capacitance of the capacitor thereby providing for a method of purifying and/or analyzing charged molecules, for example, in a solution by modifying the concentration of the fluid as it passes through the flow-through capacitor.

The flow-through capacitor of the invention may be employed in various designs provided that the solution can flow through or across the charged metal plates or layers, or ionic plates in the case of electrolytic capacitors, wherein the flow-through capacitor comprises a porous spacer layer to permit the flow of the fluid, an electrically conductive layer and a high surface area electrically conductive layer adjacent or in electrical communication with the backing layer. The flow-through capacitor may comprise a film capacitor wherein the fluid is passed between a pair of metal electrodes having an insulating, dielectric film passed between the electrodes. Some of the film-type capacitors provide for a low capacitance which may be useful for analytical purposes where small amounts of analyte is desired. However, such film capacitors have an inherently low capacitance, and therefore, a low charge holding ability. Electrolytic capacitors may also be employed and employ certain metals, such as aluminum and tantalum, which metals tend to form oxide layers which adhere tightly to the metal and which are also good insulators and constitute very thin insulating layers. The capacitance increases with the thinness of dielectric layers. Therefore, these thin oxide layers provide exceptional capacitance. In electrolytic capacitors one of the two metal plates typical of other capacitors has been replaced by an ionic solution which forms intimate contact with the oxide and reacts with the metal to form the oxide itself. Electrolytic capacitors typically use aluminum or tantalum. Aluminum tends to be soluble outside of a narrow pH frame and is readily attacked by halides and therefore is easily corroded, but its cost is low, while tantalum has a non-soluble oxide layer which is stable over a broad pH range and is also immune to corrosion. Hence, the electrolytic capacitors have a relatively high capacitance. However, the amount of capacitance needed to purify even a dilute solution is extremely large, therefore electrolytic capacitors define typical uses for purifying high purity water or protein purification where the feed stream is relatively dilute with the ionic concentrations.

The flow-through, double layer capacitor of the invention avoids the problems associated with typical thin film or electrolytic capacitors, since capacitance is inversely proportioned to the dielectric thickness and directly proportioned to electrode surface area. The flow-through capacitor of the invention employs a conductive layer with a high surface area electrically conductive material layer. In one preferred embodiment, the high surface electrically conductive layer may comprise a porous carbon fiber layer typically a porous, woven, flexible fiber cloth layer in contact with an electrically conductive backing layer, and more particularly of a flexible graphite layer which is highly electrically conductive. The high surface area electrically conductive layer may also comprise palladium or platinum black. Activated carbon may also be employed; however, in granular form, activated carbon is not a good electrical conductor unless it is in a compressed, porous form; however, compressing reduces the porosity.

One preferred embodiment of the invention comprises an active carbon fiber woven layer which provides for electrical conductivity and high porosity, although any other material which is highly electrically conductive and which has micropores can be employed for the high surface active area. For example, capacitors made with Toyobo Co. activated carbon KF cloth have 1000X the charge delivery as electrolytics (see "KF for Electro Double Layer Capacitors"[9], Toyobo Co. Bulletin, PCF 110).

For example, one material which may be employed as the high surface area layer comprises a material known as azite, a black ceramic-like substance, which is highly porous and very strong and yet electrically conductive and is composed of a synthetic carbon polymer whose structure is flat with holes (pores) (see Science[10], Jan. 12, 1990). In addition, it may be desirable to provide for a chemical modification of the high surface area electrically conductive layer by the employment of adsorbing molecules thereon to alter the electrical characteristics, such as for example, adsorbing an aromatic molecule that contains a charge group onto the carbon cloth material layer which chemical modification of the surface active area may act as an ion exchanger. Azite material consists of micropores which provide superior capacitance properties due to the elimination of one diffusion barrier, that is, macroporous and microporous layers, and is easy to fabricate. Azite material provides for a three dimensional structure and may thus be used alone in connection with merely a non-porous dielectric spacer to provide a flow-through capacitor. In addition, since the three dimensional structure of azite is flat with holes, convective flow right through the pores of the material allows a faster method of purification than other materials, such as activated carbon and platinum black, where the porosity is on the surface, and slower processes of electrodiffusion set a limit on the speed of separation.

In one embodiment of a flow-through capacitor of the invention, a spirally wound plurality of layers is adapted to be wound around a hollow central core, the central core acting as the inlet and outlet of the "chromatographic column and the central core having a plurality of holes through its length so as to permit the fluid to be separated or purified and to the non-conductive, porous spacer layer in the flow-through capacitor. The flow path may be down through the central layer or from the outside of the flow-through cartridge which is placed in the chromatographic column. Generally, the flow-through capacitor may be sealed at each end and has extending leads which are adapted to be connected to a DC-controlled power supply. The cartridge is formed by rolling up the porous spacer layer, the conductive backing layer, the conductive high surface layer, together with another conductive, porous spacer layer, a second conductive backing layer and the second conductive high surface area layer all about the central tube.

The controlled charge chromatography system may be employed for the separation of a wide variety of fluids and more particularly, any solute, solvent or liquid system that wants to be concentrated or purified by resolving into separate species. The solvent can be polar, such as water, or non-polar, such as an aromatic, which fluid contains material which has selectivity for the solid phase and which can be modulated by controlling the charge of the solid phase, that is, the high surface active layer. For example, the solution may be of deionzed water with resolved bands of ionic species, such as sodium chloride or other salts, and also any other types of molecules, organic, inorganic or biological. The invention will be disclosed for the purposes of illustration in connection with the separation of ionic liquid solutes; however, the system and method may be advantageously employed and used in the separation of other fluids, such as, but not limited to: non-ionic solutes, like hydrophobic solutes, or other fluids which contain one or more components which interact or are affected by electrically conductive surfaces, for example, liquids containing DNA, viruses, bacteria, cells, colloids or mixtures thereof. The flow-through capacitor permits the control of the charge on the stationary phase as the high surface area phase of the flow-through capacitor.

The invention will be described for the purposes of illustration only in connection with certain embodiments; however, it is recognized that those persons skilled in the art may make various modifications, changes, improvements and additions to the preferred embodiments or illustrated embodiments, all without departing from the spirit and scope of the invention.

DESCRIPTION OF THE EMBODIMENTS

Figure 1:
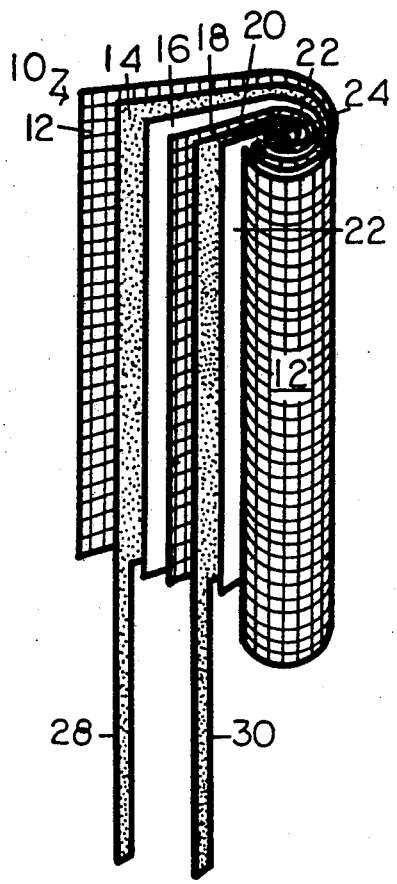
FIG. 1 is an illustrative, schematic, partially exploded view of the flow-through capacitor of the invention.
Figure 2:
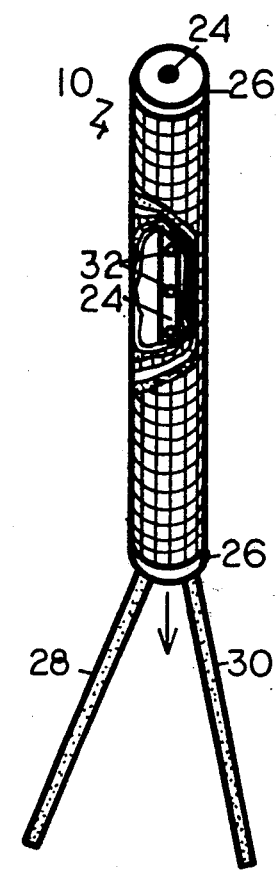
FIG. 2 is a schematic, illustrative view of the completed flow-through capacitor of the invention.

With particular reference to FIGS. 1 and 2, there is shown in FIG. 1 an exploded view of the flow-through capacitor of the invention 10 comprised of a plurality of layers wound about a central plastic tubing 24 having a plurality of perforations 32 therein extending down its length 32 and having a one end which serves an inlet for a fluid to be purified and an other end which serves as an outlet for the discharge of the purified fluid and the ionic species. Layers 12 and 18 which may be the same or different form a non-conductive porous spacer sheet material having a thickness for example of about 50 mils to 120 mils, and more particularly, a layer of nylon woven cloth which forms a non-conductive spacer material between the anode and the cathode. Layers 14 and 20 comprise a conductive backing layer which optionally may have holes punched therein to improve flow properties and which may include horizontal leaves extending therefrom to act as leads 28 and 30 for connection to a power source. For example, the conductive backing may comprise Union Carbide's Graphoil ® brand 5 mils thick graphite foil with pin holes punched therethrough. Layers 16 and 22 are comprised of a high surface area conductive material, and more particularly in the illustrated embodiment, an activated carbon woven fiber cloth to form a charge-holding, conductive high surface area (for example cloth ANF #62 from Toyobo of Japan).

FIG. 2 is a schematic illustration of the flow-through capacitor wherein the layers have been wrapped around the central core 24 wherein both ends are sealed with an epoxy resin 26 leaving open the inlet of the tube 24 and the outlet. FIG. 2 illustrates a partial sectional view that the inner core tube 24 has a series of holes 32 therein, for example, 16, 1 mm diameter holes, 1/10" apart, on a 3/16" outside diameter tubing as the core. In another embodiment, the capacitor may have no epoxy seals, and a solid tube for a central core, so the flow is between the layers. The capacitor may have the top end of the hollow tube sealed shut so that the direction of flow is through the sides of the device, through the successive layers, and then out the open end of the inner hollow tube.

Figure 3:
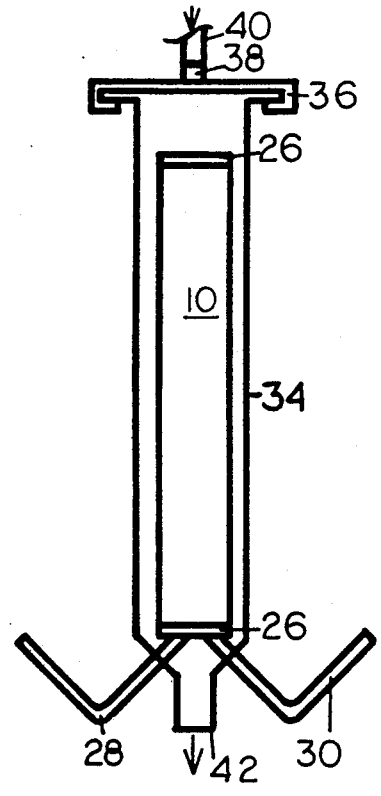
FIG. 3 is a schematic, illustration of a chromatographic column employing the flow-through capacitor of the invention.

FIG. 3 is an illustration of chromatographic column 34 containing the flow-through capacitor 10 disposed therein and generally axially aligned with the axis of the column 34, the column having an end cap 36, an inlet 38 and connected to a tubing 40 for the introduction of a fluid material to be purified, the end cap gasketed to a defined pressure, for example, 100 psi, and the column 34 having an outlet 42. Extending from the column 34 are the conductive leads 28 and 30 which have epoxy seals where the outlet tubing 50 and the Graphoil leads 28 and 30 come through column 34. For example, the column 34 may comprise a transparent, plastic, polypropylene, syringe-type barrel.

Figure 4:
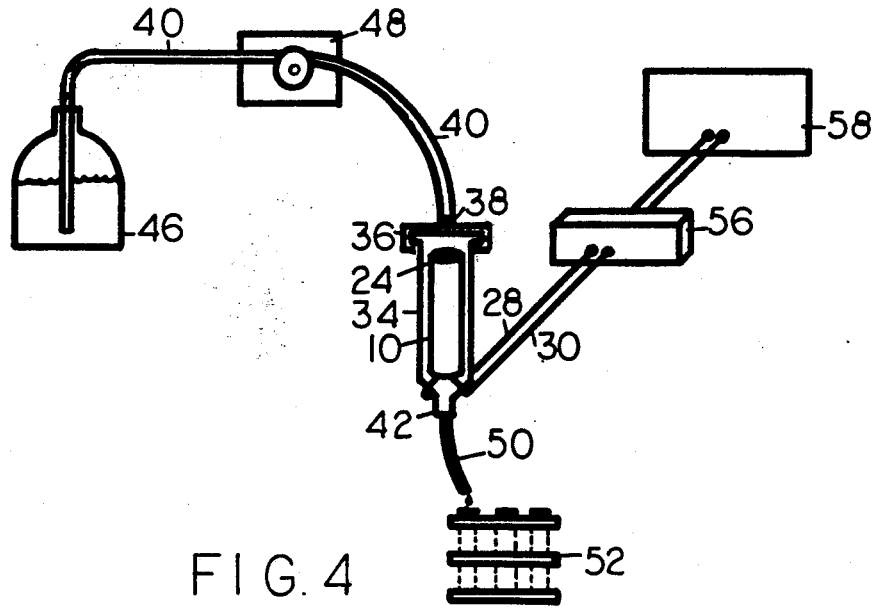
FIG. 4 is a schematic illustration of a controlled charge ionic purification chromatography system and method of the invention.

FIG. 4 is a schematic illustration of a controlled charge purification chromatography system and includes a source of fluid, such as a solution source 46, inlet tubing 40 which passes through a pump 48 to connect the fluid into the inlet 38 of the end cap 36 of the chromatographic column 34 which contains the flow-through capacitor 10 wherein the leads 28 and 30 from the capacitor 10 are connected to an electric control system 56 which programs and controls the voltage, the off/on cycles, voltage gradients and permits reversal of polarity and otherwise controls the electric power to the flow through capacitor through a 24-volt DC power supply 58. The outlet from the column 34 is through outlet 42 through a tube 50 which directs the material or the elution to a rotating-type fraction collector schematically illustrated as 52. The outlet 42 may have an on/off fluid control valve.

The chromatographic system as illustrated in FIG. 4 may be employed to provide for the purification of a variety of solutions containing ionic material, and for example, the purification of a 0.01 molar sodium chloride aqueous solution from feed 46 which is fed by pump 48 through tubing 40 into the inlet 38 of the end 36 to the column 34 and hence, through 24 into the flow through capacitor 10 which has a controlled charge thereon of about 2 volts. The sodium chloride feed solution is purified to a $1 \times 10^{-4}$ molar at a flow rate of 0.23 ml/minute from the outlet 42 through control valve 60 into the tubing 50 into the fraction collector 52, while 2 volts are also supplied to the DC power supply through logic 56 to leads 28 and 30 to provide a flow through capacitor. The purified sodium chloride solution was recovered simply by shorting the leads 28 and 30. In other examples, much larger peak or outlet was obtained from a $5 \times 10^{-4}$ molar purified outlet to a 0.05 molar outlet peak by reversing the polarity of the leads 28 and 30 for about 5 seconds. The flow rates may vary; however in purification experiments with sodium chloride, the flow rates vary from 0.23 ml per minute to 3 ml per minute or more.

Thus, as illustrated a new, improved and unique controlled charge purification chromatography column system and method has been discovered which provides for the effective and rapid separation by a flow through capacitor of high electric capacitance and high surface area, high adsorption ability, electrically conductive, stationary phase in the chromatographic column.

REFERENCES

[1] Bassler, Barbara and Hartwick, Richard, "Electrically Conductive Stationary Phases for HPLC", Abstract from AICHE Meeting, San Francisco, Calif., Nov. 5-10, 1989

[2] Antrim, Robert; Scherrer, Robert and Yacynych, Alexander, "Electrochromatography—A Preliminary Study of the Effect of Applied Potential On a Carbonaceous Chromatographic Column", *Anal. Chim. Acta.* 164 (1984) 283

[3] Blaedel, W. J. and Strohl, J. H., "Continuous Quantitative Electrolysis", *Anal. Chem.*, Vol. 36, No. 7, Jun., 1964, pp. 1245-1251

[4] Strohl, John and Polutanovich, Thomas, "A Packed Graphite Cell for Thin-Layer Chromatography", *Analytical Letters*, 2(8), pp. 423-431 (1969)

[5] Fujinaga, Taitiro, "Electrolytic Chromatography and Coulometric Detection With the Column Electrode", *Pure Applied Chemistry*, 25 (1971) pp. 709-726

[6] Hern, James and Strohl, John H., "Modified Graphites for Chelation and Ion Exchange", *Analytical Chemistry*, Vol. 50, No. 14, Dec., 1978, pp. 1954-1959

[7] Stoner, G. and Srinivasan, S., "Absorbtion of Blood Proteins on Metals Using Capacitance Techniques", *Journal of Physical Chemistry*, Vol. 74, No. 5, pp. 1088-1094, Mar. 5, 1970

[8] Newman, Arnold L., "Sintered Pellet with Biochemically Active Layer", U.S. Pat. No. 4,769,191, Sep. 6, 1988

[9] "KF for Electro Double Layer Capacitors", Toyobo Co. Bulletin, PCF 110

[10] Waldrop, M. Mitchell, *Science*, Vol. 247, No. 4939, Jan. 12, 1990, p. 161

I claim:

1. A chromatographic column for the controlled charge purification of a fluid, which column comprises:
    a) an inlet at the one end of the column for the introduction of a fluid containing at ionic material to be purified;
    b) an outlet at the other end of the column for the discharge of a purified ionic material; and
    c) a flow-through capacitor disposed in the column between the inlet and the outlet and generally axially aligned with the axis of the column which capacitor comprises a spirally wound plurality of spaced apart layers including:
        i) a first electrically conductive backing layer;
        ii) a first high surface area electrically conductive layer to act as the stationary phase of the chromatographic column;
        iii) a first non-conductive, porous spacer layer to permit the flow of fluid;
        iv) a second electrically conductive backing layer;
        v) a second high surface area electrically conductive layer to act as a stationary phase of the chromatographic column; and
        vi) a second non-conductive porous spacer layer, the layers spirally wound so as to permit the flow of fluid generally axially through the spirally wound flow-through capacitor through the non-conductive, porous spacer layers from the one to the other end, and which flow-through capacitor contains first and second anode and cathode leads adapted to be connected to a power supply to provide for the conductive first and second backing to become the anode and cathode of the flow-through capacitor.

2. The column of claim 1 wherein the non-conductive, porous spacer layer comprises a synthetic, woven fiber material.

3. The column of claim 1 wherein the electrically conductive backing layer comprises a conductive film layer selected from a group consisting of: aluminum; tantalum; and graphite.

4. The column of claim 1 wherein the high surface area conductive layer comprises compressed, activated carbon particles.

5. The column of claim 1 wherein the high surface area conductive layer comprises activated carbon wove fibers.

6. The column of claim 1 wherein the high surface area conductive layer comprises electrodeposited platinum series black.

7. The column of claim 1 wherein the high surface area conductive layer comprises azite.

8. The column of claim 1 which includes a central tube having a one and an other end, one end being the inlet, the other end being the outlet, the tube having a plurality of holes therein and the first and second layers wound about the tube to form the spirally wound capacitor and the ends of the tubes sealed with a resin material.

9. The chromatographic column of claim 1 wherein the capacitor has a capacitance of over 1000 farads capacitance.

10. The chromatographic column of claim 1 wherein the first or second conductive backing layers or both have a plurality of holes therein to improve flow.

11. The chromatographic column of claim 1 wherein the first and second non-conductive porous spacer layer has a thickness of 50 to 120 mils and comprises a nylon woven cloth; the first and second conductive backing layers comprising a graphite foil layer; and the first and second high surface area conductive layers comprising an activated carbon woven fiber cloth.

12. A chromatographic system which includes the chromatographic column of claim 1 and which also includes a DC power source; an electrical connecting means between the DC power source to the electrically conductive leads of the capacitor; a source of fluid to be purified; a means to introduce the fluid from the source into the inlet of the chromatographic column; and a fraction collection means to collect the purified material from the outlet of the chromatographic column.

13. The chromatographic system of claim 12 which includes a logic control electrically connected to the DC power supply and the capacitor to provide for control and direction of the voltage.

14. A chromatographic column for the controlled charge purification of a liquid, which column comprises:
   a) an inlet at the one end of the column for the introduction of a liquid to be purified;
   b) an outlet at the other end of the column for the discharge of a purified liquid and concentrated materials;
   c) a flow-through capacitor disposed in the column between the inlet and the outlet and generally axially aligned with the axis of the column which capacitor comprises:
      i) a plurality of adjacent layers of a first spacer layer, a first backing layer, a first surface area layer, a second spacer layer, a second backing layer and a second surface area layer, the first and second spacer layers comprising a non-electrically conductive porous spacer layer to permit the flow of liquid therethrough; said first and second backing layers comprising a firs and second electrically conductive backing layer; said first and second surface area layers comprising a high surface area electrically conductive layer to act as the stationary phase of the chromatographic column; and
      ii) an anode and a cathode lead connected respectively to the first and second backing layers, which anode and cathode leads are adapted to be connected to a DC power source to provide separate and opposite electrical charges on the first and second backing layers.

15. The column of claim 14 wherein the non-conductive, porous spacer layer comprises a synthetic, woven fiber material.

16. The column of claim 14 wherein the electrically conductive backing layer comprises a conductive film layer selected from a group consisting of: aluminum, tantalum and graphite.

17. The column of claim 14 wherein the high surface area conductive layer comprises compressed, activated carbon particles.

18. The column of claim 14 wherein the high surface area conductive layer comprises activated carbon woven fibers.

19. The column of claim 14 wherein the high surface area conductive layer comprises electrodeposited platinum series black.

20. The column of claim 14 wherein the first, second or both backing layers have holes therein for flow of liquid therethrough.

21. The column of claim 14 wherein the layers are spirally wound about a central, perforated, plastic tube and the ends of the spirally wound capacitor sealed.

22. A chromatographic system which includes the column of claim 14 and a DC power source connected to the anode and cathode leads of the capacitor.

23. The system of claim 22 which includes a logic means to control voltage, on/off cycles, voltage gradients and to reversal of polarity of the DC source.

24. The system of claim 22 which includes:
   a) a source of liquid to be purified which liquid contains ionic material;
   b) pump means to pump the liquid from the source into the inlet of the column; and
   c) a fraction collector means to collect purified liquid and materials from the outlet of the column.

25. The column of claim 14 wherein the liquid to be purified comprises water-containing ionic salt material.

26. The column of claim 14 wherein the capacitor includes a first and second spacer layer of porous, woven cloth, a first and second backing layer of flexible graphite foil with hole therein, and a first and second surface area layers of activated carbon, woven fiber cloth.

27. The column of claim 14 which includes a separate end sealed, spirally wound capacitor cartridge with the anode and cathode leads extending outside of the column.

* * * * *

UNITED STATES PATENT AND TRADEMARK OFFICE
CERTIFICATE OF CORRECTION

PATENT NO. : 5,196,115

DATED : March 23, 1993

INVENTOR(S) : Marc D. Andleman

It is certified that error appears in the above-identified patent and that said Letters Patent is hereby corrected as shown below:

column 8, line 54, delete "wove" and insert --woven--.

Signed and Sealed this

Fourth Day of January, 1994

Attest:

BRUCE LEHMAN

*Attesting Officer*    *Commissioner of Patents and Trademarks*